(12) United States Patent
Malofsky et al.

(10) Patent No.: US 6,245,933 B1
(45) Date of Patent: Jun. 12, 2001

(54) TRANSESTERIFICATION METHOD FOR MAKING CYANOACRYLATES

(75) Inventors: Bernard Malofsky, Bloomfield, CT (US); Ibraheem T. Badejo, Morrisville, NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 09/443,298

(22) Filed: Nov. 19, 1999

(51) Int. Cl.$^7$ .................... C07C 255/23; C07C 253/30
(52) U.S. Cl. .................... 558/381; 558/375; 558/443
(58) Field of Search ..................... 558/443, 375, 558/381

(56) References Cited

U.S. PATENT DOCUMENTS

| | | |
|---|---|---|
| 2,721,858 | 10/1955 | Joyner et al. . |
| 2,756,251 | 7/1956 | Joyner et al. . |
| 2,763,677 | 9/1956 | Jeremias . |
| 3,559,652 | 2/1971 | Banitt et al. . |
| 3,759,264 | 9/1973 | Coover, Jr. et al. . |
| 3,975,422 | 8/1976 | Buck . |
| 4,012,402 | 3/1977 | Buck . |
| 4,321,180 | 3/1982 | Kimura et al. . |
| 4,364,876 | 12/1982 | Kimura et al. . |
| 5,175,337 | 12/1992 | Mikuni et al. . |
| 5,359,101 | 10/1994 | Woods et al. . |
| 5,504,252 | 4/1996 | Klemarczyk . |
| 5,582,834 | 12/1996 | Leung et al. . |
| 5,624,669 | 4/1997 | Leung et al. . |
| 5,637,752 | 6/1997 | Nakamura et al. . |
| 5,703,267 | 12/1997 | Takahashi et al. . |
| 6,057,472 | * 5/2000 | Sailhan et al. .................... 558/381 |

FOREIGN PATENT DOCUMENTS

| | | |
|---|---|---|
| 726086 | 4/1980 | (SU) . |
| WO 95/33708 | 12/1995 | (WO) . |

* cited by examiner

*Primary Examiner*—Michael G. Ambrose
*Assistant Examiner*—Ebenezer Sacket
(74) *Attorney, Agent, or Firm*—Oliff & Berridge, PLC

(57) ABSTRACT

An α-cyanoacrylate may be formed by first condensing a cyanoacetate with paraformaldehyde or formaldehyde; reacting the polymer formed with an alcohol to transesterify the polymer; and depolymerizing the polymer to form α-cyanoacrylate monomers.

20 Claims, No Drawings

TRANSESTERIFICATION METHOD FOR MAKING CYANOACRYLATES

BACKGROUND OF THE INVENTION

1. Field of Invention

The invention relates to a method for making cyanoacrylates.

2. Description of Related Art

Monomer and polymer adhesives are both used in industrial (including household) and medical applications. Included among these adhesives are 1,1-disubstituted ethylene monomers and polymers, such as α-cyanoacrylates. Since the discovery of the adhesive properties of such monomers and polymers, they have found wide use due to the speed with which they cure, the strength of the resulting bond formed, and their relative ease of use. These characteristics have made α-cyanoacrylate adhesives the primary choice for numerous applications such as bonding plastics, rubbers, glass, metals, wood, and, more recently, biological tissues.

Medical applications of 1,1-disubstituted ethylene adhesive compositions, such as α-cyanoacrylate compositions, include use as an alternate and an adjunct to surgical sutures and staples in wound closure as well as for covering and protecting surface wounds such as lacerations, abrasions, burns, stomatitis, sores, and other surface wounds. When an adhesive is applied, it is usually applied in its monomeric form, and the resultant polymerization gives rise to the desired adhesive bond.

U.S. Pat. No. 5,624,669 to Leung et al. describes a process for making cyanoacrylates. In the method, α-cyanoacrylates are prepared by condensing a cyanoacetate and either formaldehyde or paraformaldehyde in the presence of a catalyst at a molar ratio of 0.5–1.5:1 to obtain a condensate; depolymerizing the condensation reaction mixture either directly or after removal of the condensation catalyst to yield crude cyanoacrylate; and distilling the crude cyanoacrylate to form a high purity cyanoacrylate. In order to prepare a particular α-cyanoacrylate, the '669 patent discloses making a corresponding cyanoacetate by esterifying cyanoacetic acid with the corresponding alcohol or by transesterifying an alkyl cyanoacetate with the corresponding alcohol before the cyanoacetate undergoes the condensation reaction with the formaldehyde or paraformaldehyde.

U.S. Pat. No. 4,364,876 to Kimura et al. describes reaction conditions for forming α-cyanoacrylates by the method described in the '669 patent.

U.S. Pat. No. 2,721,858 to Joyner et al. and U.S. Pat. No. 2,763,677 to Jeremias et al. also describe reaction conditions for forming α-cyanoacrylates from the corresponding cyanoacetate.

As used herein the terms "corresponding" or "corresponds" with reference to a cyanoacetate and an α-cyanoacrylate means that the same R group is attached to oxygen of the carboxyl group in the two compounds. Thus, methylcyanoacetate corresponds to methyl α-cyanoacrylate. The term "corresponding alcohol," as used herein, refers to an alcohol having the same R group attached to the hydroxyl group as the corresponding cyanoacetate or α-cyanoacrylate has attached to the oxygen of the carboxy group. Thus, methyl alcohol corresponds to methylcyanoacetate and to methyl α-cyanoacrylate.

In all of the above mentioned references, the cyanoacetate that undergoes the condensation reaction corresponds to the α-cyanoacrylate that is obtained.

U.S. Pat. No. 5,637,752 to Nakamura et al. describes reaction conditions for the transesterification of a lower alkyl cyanoacetate with an alcohol to form a higher alkyl cyanoacetate.

SU 726,086 describes a process for producing α-cyanoacrylates by reacting ethyl α-cyanoacrylate monomer with excess alcohol in the presence of an acid or metal chloride catalyst. The process is simplified and polymerization of the final product is prevented by conducting the transesterification reaction at 100–140° C. in the presence of sulfuric or para-toluene sulfonic acid or zinc chloride catalyst.

U.S. Pat. No. 2,756,251 to Joyner et al. describes a method for depolymerizing polymeric α-cyanoacrylates.

SUMMARY OF THE INVENTION

The parameters for conducting a condensation reaction of methyl or ethyl cyanoacetate with formaldehyde or paraformaldehyde to form methyl or ethyl α-cyanoacrylate, respectively, with maximum yield are well established. However, the parameters for the condensation of other cyanoacetates to form other α-cyanoacrylates are not as well established. In addition, due to steric considerations, it is difficult to polymerize higher alkyl cyanoacetates and the reaction generally results in smaller oligomers. When cracking an oligomer, the last two monomers, which are joined as cyanoglutarate, are generally difficult to crack. Thus, if a greater number of smaller oligomers are formed, then more of the starting material monomers may be lost. As a result, the final yield of monomers from the overall process may not be as ideal as with methyl or ethyl cyanoacetates. Therefore, it is advantageous to form α-cyanoacrylates other than methyl and ethyl α-cyanoacrylates using processes that do not require the condensation of cyanoacetates other than methyl and ethyl cyanoacetates.

The present invention provides a process for forming α-cyanoacrylates, particularly α-cyanoacrylates of formula (I) where $R^1$ is a carbon containing organic group other than a methyl or ethyl group:

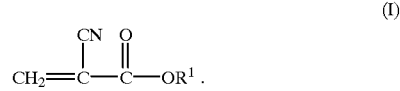

The process comprises reacting a particular cyanoacetate, particularly methyl or ethyl cyanoacetate, with paraformaldehyde or any other convenient form of formaldehyde to prepare an α-cyanoacrylate oligomer or polymer. The cyanoacrylate oligomer or polymer condensation product is then transesterified with an alcohol to form a different cyanoacrylate oligomer or polymer before undergoing a depolymerization to form the target α-cyanoacrylate. The process may be demonstrated in the following reaction scheme:

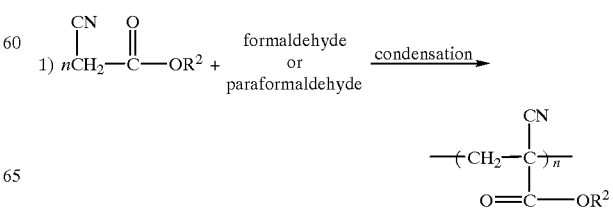

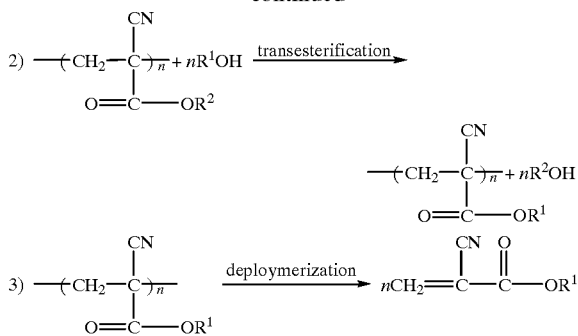

In this reaction scheme, $R^1$ and $R^2$ both represent any carbon containing organic group as long as they are different from one another. Preferably, n is from 2 to 100.

Although an embodiment of the invention is directed to a process in which $R^2$ is a methyl or ethyl group and $R^1$ is a group other than a methyl or ethyl group, the present invention is not limited to such an embodiment. Thus, $R^2$ may be a group other than a methyl or ethyl group and/or $R^1$ may be a methyl or ethyl group.

By conducting the transesterification reaction after the condensation reaction, better yield can be obtained. In particular, by using lower alkyl cyanoacetates, longer oligomers or polymers may be obtained, which results in higher yield during the cracking reaction. In addition, because it is not necessary to use the corresponding cyanoacetate to form particular α-cyanoacrylate monomers, a different cyanoacetate for which optimal condensation conditions are more well established and/or more readily available may be effectively used to produce the particular α-cyanoacrylate monomers at relatively high yield.

DETAILED DESCRIPTION OF PREFERRED EMBODIMENTS

The process of the present invention comprises reacting a particular cyanoacetate, particularly methyl or ethyl cyanoacetate, with paraformaldehyde or any other convenient form of formaldehyde to prepare an α-cyanoacrylate oligomer or polymer. Conditions for achieving this condensation reaction are known in the art. In particular, U.S. Pat. No. 5,624,669 to Leung et al., U.S. Pat. No. 4,364,876 to Kimura et al., U.S. Pat. No. 2,721,858 to Joyner et al. and/or U.S. Pat. No. 2,763,677 to Jeremias et al., each of which is hereby incorporated herein by reference, describe conditions for the condensation reaction.

As used herein the term "formaldehyde" is intended to include any source of formaldehyde that may be used to achieve the condensation reaction of the present invention including formaldehyde itself, as well as polymers thereof, such as paraformaldehyde or the like, and aqueous solutions of formaldehyde, such as formalin.

The cyanoacrylate oligomer or polymer formed generally contains from about 2 to 100 cyanoacrylate monomer units. However polymers having a larger number of cyanoacrylate monomers may also be formed. Preferably, the cyanoacrylate oligomer or polymer contains from 3 to 75, more preferably from 5 to 50, and even more preferably from 10 to 50, cyanoacrylate monomers.

The condensation may be conducted in an organic solvent. Preferably, the solvent forms an azeotropic mixture with water. Exemplary solvents include toluene, hexane, pentane, benzene, cyclohexane, heptane, octane, nonane, xylenes, carbon tetrachloride and ethylbenzene. During the condensation reaction, the solution may be heated to the azeotropic point. By such heating, the water may be selectively removed from the reaction medium.

In an embodiment of the present invention, the condensation reaction is conducted in the presence of one or more basic condensation catalysts. However, one or more acidic condensation catalysts may alternatively be used. Basic catalysts that may be used include, but are not limited to, pyridine; alkali metal or alkaline earth hydroxide, carbonate or bicarbonates, such as sodium hydroxide, potassium hydroxide, sodium carbonate, sodium bicarbonate; metal alcoholates, such as sodium methoxide and potassium t-butoxide; trialkylamines, such as triethylamine; dialkylamines, such as dimethylamine; alkylamines, such as methylamine; and primary and secondary amines, such as piperidine, as well as salts of the various amines. Acidic catalysts that may be used include, but are not limited to, acetic acid, piperidine hydrochloride and Lewis acids, such as zinc chloride or titanium tetrachloride. In addition to more traditional acid and basic catalysts, the condensation reaction can be conducted in the presence of an acidic or basic ion-exchange resin, such as an acidic or basic DOWEX ion-exchange resin manufactured and sold by Dow Chemical, Midland, Mich.

The cyanoacrylate oligomer or polymer condensation product is then transesterified with an alcohol to form a different cyanoacrylate oligomer or polymer. The solvent used for the condensation reaction may or may not be removed from the reaction medium before the transesterification reaction. The alcohol is generally added in molar excess, such as in an amount of from 1.5 to 2.0 moles per cyanoacrylate monomer unit in the oligomer or polymer to drive the transesterification reaction. To transesterify the oligomer or polymer, the reaction medium is generally heated. It may be heated to a temperature above the boiling point of the alcohol produced in the reaction to concurrently remove the alcohol being produced. Alternatively or in addition, it is possible to add a molecular sieve to remove the alcohol produced and help drive the reaction.

The transesterification reaction may be conducted in the presence of a strong acid (Bronsted acid) catalyst or an organometallic catalyst. Acidic catalysts that may be used include, but are not limited to, p-toluenesulfonic acid, hydrochloric acid, trifluoroacetic acid and Lewis acids, such as boron trifluoride and zinc chloride. Organometallic catalysts that may be used include, but are not limited to, titanium tetraisopropoxide, such as the product sold under the trademark TYZOR TPT by DuPont, aluminum isopropoxide, tributyltin oxide and sumarium isopropoxide.

The transesterification reaction may also be conducted in the presence of metal alcoholate (alkali metal alcoholate or alkaline earth alcoholate), such as potassium 2-octoxide or sodium 2-octoxide. The type of metal alkoxide to be used depends on the alcohol used in the reaction. For example, the transesterification of ethylcyanoacrylate oligomer or polymer to 2-octylcynoacrylate oligomer or polymer may be conducted with sodium 2-octoxide. It is also possible to use sodium ethoxide for the transesterification of ethylcyanoacrylate oligomer or polymer to 2-octylcynoacrylate oligomer or polymer. In addition, the transesterification may be conducted in the presence of an acidic or basic ion-exchange resin, such as an acidic or basic DOWEX ion-exchange resin manufactured and sold by Dow Chemical, Midland, Mich.

In a particular embodiment, a methyl or ethyl α-cyanoacrylate oligomer or polymer is transesterified with an alcohol other than methyl or ethyl alcohol to form an α-cyanoacrylate oligomer or polymer other than methyl or ethyl α-cyanoacrylate oligomer or polymer. Preferably the alcohol transesterified with the oligomer or polymer has four or more carbons.

Since the alcohol is generally added in molar excess, it is generally necessary to remove the excess alcohol after the transesterification process. In addition, since the second stage of the reaction may be conducted in a solvent in addition to the alcohol, it may also be necessary to remove other solvent after the transesterification. Thus, after completing the transesterification, in embodiments of the invention, the solvent and/or excess alcohol are removed, such as by stripping the polymer under a vacuum.

The transesterified cyanoacrylate oligomer or polymer then undergoes a depolymerization to form the α-cyanoacrylate. The depolymerization may be conducted by processes known in the art, such as by the processes described in U.S. Pat. No. 5,624,669 to Leung et al., U.S. Pat. No. 4,364,876 to Kimura et al. and/or U.S. Pat. No. 2,756,251 to Joyner et al., each of which is incorporated herein by reference. In particular, the polymer may be heated to a sufficiently high temperature, such as a temperature of from 100° C. to 200° C., to crack the oligomer or polymer.

The cracking process should be conducted in an anhydrous environment. The cracking process may be conducted in the presence of a dehydrant, such as polyphosphoric acid or phosphorus pentoxide ($P_2O_5$), to keep the environment anhydrous. In addition, the cracking process may be conducted in the presence of a radical scavenger, such as copper chloride, hydroquinone or any hindered phenolic radical scavenger.

In the above-mentioned reaction scheme, $R^2$ may be any carbon containing organic group, such as an alkyl group having 1–16 carbon atoms, but is preferably a methyl or ethyl group, more preferably an ethyl group.

$R^1$ is preferably any carbon containing organic group other than a methyl or ethyl group. For example, $R^1$ may be a hydrocarbyl or substituted hydrocarbyl group; a group having the formula —$R^4$—O—$R^5$—O—$R^6$ or the formula —$R^5$—O—$R^6$, where $R^4$ is a 1,2-alkylene group having 2–4 carbon atoms, $R^5$ is an alkylene group having 2–4 carbon atoms, and $R^6$ is an alkyl group having 1–6 carbon atoms; or a group having formula

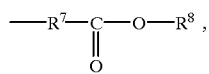

wherein $R^7$ is

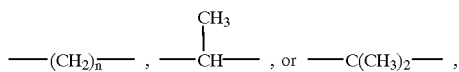

wherein n is 1–10, preferably 1–5, and $R^8$ is an organic moiety.

Examples of suitable hydrocarbyl and substituted hydrocarbyl groups include straight chain or branched chain alkyl groups having 1–16 carbon atoms; straight chain or branched chain $C_1$–$C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic moiety $R^8$ may be substituted or unsubstituted and may be straight chain, branched or cyclic, saturated, unsaturated or aromatic. Examples of such organic moieties include $C_1$–$C_8$ alkyl moieties, $C_2$–$C_8$ alkenyl moieties, $C_2$–$C_8$ alkynyl moieties, $C_3$–$C_{12}$ cycloaliphatic moieties, aryl moieties such as phenyl and substituted phenyl and aralkyl moieties such as benzyl, methylbenzyl, and phenylethyl. Other organic moieties include substituted hydrocarbon moieties, such as halo (e.g., chloro-, fluoro- and bromo-substituted hydrocarbons) and oxy-substituted hydrocarbon (e.g., alkoxy substituted hydrocarbons) moieties. Preferred organic radicals are alkyl, alkenyl, and alkynyl moieties having from 1 to about 8 carbon atoms, and halo-substituted derivatives thereof. Particularly preferred are alkyl moieties of 4 to 6 carbon atoms.

In embodiments of the invention, $R^1$ is preferably an alkyl group having 1–10 carbon atoms or a group having the formula —$AOR^9$, wherein A is a divalent straight or branched chain alkylene or oxyalkylene moiety having 2–8 carbon atoms, and $R^9$ is a straight or branched alkyl moiety having 1–8 carbon atoms.

Examples of groups represented by the formula —$AOR^9$ include 1-methoxy-2-propyl, 2-butoxy ethyl, isopropoxy ethyl, 2-methoxy ethyl, and 2-ethoxy ethyl.

Preferred α-cyanoacrylates produced by the method of the present invention are alkyl α-cyanoacrylates other than methyl and ethyl α-cyanoacrylates, including octyl cyanoacrylate, such as 2-octyl cyanoacrylate; dodecyl cyanoacrylate; 2-ethylhexyl cyanoacrylate; butyl cyanoacrylate such as n-butyl, iso-butyl or t-butyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate. More preferred monomers are n-butyl and 2-octyl α-cyanoacrylate. Monomers used for medical purposes in the present application should be very pure and contain few impurities (e.g., surgical grade). Monomers utilized for industrial purposes need not be as pure.

The following examples illustrate specific embodiments of the present invention. One skilled in the art will recognize that the appropriate reagent, component ratio/concentrations may be adjusted as necessary to achieve specific product characteristics.

EXAMPLE I

A reaction flask fitted with a stirrer, a thermocouple, a Dean-Stark trap and a condenser is charged with 100 mL of toluene, 113.1 g of ethylcyanoacetate, 1.3 mL of acetic acid, 31.9 g of paraformaldehyde (96–98%) and 0.79 g of piperidine hydrochloride. The reaction medium is heated to 90° C. over 38 minutes and held at this temperature for two hours to condense the ethylcyanoacetate. During the reaction, 15 mL of water is collected. Then, the reaction medium is cooled to room temperature and maintained at room temperature overnight.

Thereafter, 300 mL of toluene, 19.02 g of p-toluenesulfonic acid and 261 g of 2-octanol are added. The reaction medium is heated to reflux to transesterify the polymer. During the reflux reaction, ethanol generated from the transesterification is allowed to boil off and is thus removed. Because toluene is boiled off with the ethanol, 2000 mL of toluene is added over the course of the reflux reaction. After the reflux reaction, the reaction medium is cooled to room temperature.

A Dean-Stark trap is then removed, and the reaction flask is set-up for vacuum distillation. By vacuum distillation, the toluene is stripped from the reaction medium. Then, 20.8 g of polyphosphoric acid and 1.0 g of copper chloride are added and the reaction medium is heated to 185° C. to crack the polymer to give 45.6 g of crude 2-octyl α-cyanoacrylate monomer.

EXAMPLE II

A reaction flask fitted with a stirrer, a thermocouple, a Dean-Stark trap and a condenser is charged with 100 mL of toluene, 114.0 g of ethylcyanoacetate, 1.3 mL of acetic acid, 32.0 g of paraformaldehyde (96–98%) and 0.79 g of piperidine hydrochloride. The reaction medium is heated to 90° C. over 18 minutes and held at this temperature for two hours to condense the ethylcyanoacetate. During the reaction, 15 mL of water is collected. Then, the reaction medium is cooled to room temperature and maintained at room temperature overnight.

Thereafter, 300 mL of toluene, 14.82 g of p-toluenesulfonic acid and 261.4 g of 2-octanol are added. The reaction medium is heated to reflux and the reflux is maintained for 5 hours and 30 minutes to transesterify the polymer. During the reflux reaction, ethanol generated from the transesterification is allowed to boil off and is thus removed. Because toluene is boiled off with the ethanol, 2000 mL of toluene is added over the course of the reflux reaction. After the reflux reaction, the reaction medium is cooled to room temperature.

A Dean-Stark trap is then removed, and the reaction flask is set-up for vacuum distillation with a vigreux column. By vacuum distillation at a temperature of from 20.3 to 126.4° C. (2.02–8.44 mmHg of pressure), the toluene is stripped from the reaction medium. Then, 23.6 g of polyphosphoric acid and 1.0 g of copper chloride are added and the reaction medium is heated to 227.3° C. to crack the polymer to give 72.3 g of crude 2-octyl α-cyanoacrylate monomer.

EXAMPLE III

A reaction flask fitted with a stirrer, a thermocouple, a Dean-Stark trap and a condenser is charged with 100 mL of toluene, 113.1 g of ethylcyanoacetate, 1.3 mL of acetic acid, 31.9 g of paraformaldehyde (96–98%) and 0.79 g of piperidine hydrochloride. The reaction medium is heated to 91.6° C. over 31 minutes and held at a temperature between 89.9 and 93.3° C. for two hours to condense the ethylcyanoacetate. During the reaction, 15 mL of water is collected. Then, 300 mL of xylene is added and the reaction temperature is increased to 130° C. and held at this temperature for three hours to remove an additional 3 mL of water.

Thereafter, 261.4 g of octanol is added to the reaction medium. Then the Dean-Stark trap is replaced with a condenser for distillation and the reaction medium is heated to 150° C. to distill off toluene and xylene. Then, the reaction medium is cooled to 90° C. Thereafter, 28 g of titanium tetraisopropoxide (TYZOR TPT™) is added. The reaction medium is heated to 200° C. When the system reaches a reaction temperature of 120° C., ethanol is distilled off. Once the temperature of the reaction medium reaches 200° C., it is maintained at this temperature for two hours to transesterify the oligomer. Then the reaction medium is cooled to room temperature.

The reaction flask is set-up for vacuum distillation. By vacuum distillation at 88° C. (1.40–2.55mmHg), the unreacted octanol is stripped from the reaction medium. Then, 32.0 g of polyphosphoric acid and 1.0 g of copper chloride are added and the reaction medium is heated between 138.7 and 176.6° C. (1.14–400 mmHg) to crack the polymer to give 75.6 g of crude 2-octyl α-cyanoacrylate monomer.

What is claimed is:

1. A method for making α-cyanoacrylates, comprising:
   reacting a cyanoacetate with paraformaldehyde or formaldehyde to form a cyanoacrylate oligomer or polymer;
   reacting the cyanoacrylate oligomer or polymer with an alcohol to transesterify the cyanoacrylate oligomer or polymer; and
   depolymerizing the transesterified cyanoacrylate oligomer or polymer to form α-cyanoacrylates.

2. The method of claim 1, wherein said cyanoacetate is methyl or ethyl cyanoacetate.

3. The method of claim 2, wherein said cyanoacetate is ethyl cyanoacetate.

4. The method of claim 1, wherein the cyanoacrylate formed is an α-cyanoacrylate other than methyl or ethyl cyanoacrylate.

5. The method of claim 1, wherein said alcohol has the formula $R^1$—OH, wherein $R^1$ is selected from the group consisting of a hydrocarbyl group; a substituted hydrocarbyl group; a group having the formula —$R^4$—O—$R^5$—O—$R^6$ or the formula —$R^5$—O—$R^6$, where $R^4$ is a 1,2-alkylene group having 2–4 carbon atoms, $R^5$ is an alkylene group having 2–4 carbon atoms, and $R^6$ is an alkyl group having 1–6 carbon atoms; and a group having formula

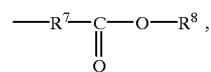

wherein $R^7$ is

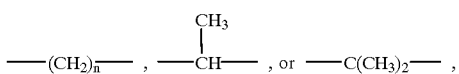

wherein n is 1–10, and $R^8$ is an organic moiety.

6. The method of claim 5, wherein said hydrocarbyl and substituted hydrocarbyl groups are selected from the group consisting of straight chain or branched chain alkyl groups having 1–16 carbon atoms; straight chain or branched chain $C_1$–$C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

7. The method of claim 1, wherein said alcohol has the formula $R^1$—OH, wherein $R^1$ is selected from the group consisting of an alkyl group having 1–10 carbon atoms and a group having the formula —$AOR^9$, wherein A is a divalent straight or branched chain alkylene or oxyalkylene moiety having 2–8 carbon atoms, and $R^9$ is a straight or branched alkyl moiety having 1–8 carbon atoms.

8. The method of claim 7, wherein said group having the formula —$AOR^9$ is selected from the group consisting of 1-methoxy-2-propyl, 2-butoxy ethyl, isopropoxy ethyl, 2-methoxy ethyl and 2-ethoxy ethyl.

9. The method of claim 1, wherein said cyanoacrylate formed is selected from the group consisting of octyl cyanoacrylate; dodecyl cyanoacrylate; 2-ethylhexyl cyanoacrylate; butyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate.

10. The method of claim 9, wherein said cyanoacrylate formed is n-butyl α-cyanoacrylate or 2-octyl α-cyanoacrylate.

11. The method of claim 1, wherein said cyanoacrylate oligomer or polymer comprises 2 to 100 monomer units.

12. The method of claim 11, wherein said cyanoacrylate oligomer or polymer comprises 3 to 75 monomer units.

13. The method of claim 11, wherein said cyanoacrylate oligomer or polymer comprises 10 to 50 monomer units.

14. The method of claim 1, wherein the transesterification is conducted in the presence of an organometallic catalyst.

15. The method of claim 14, wherein said organometallic catalyst is selected from the group consisting of titanium tetraisopropoxide, aluminum isopropoxide, tributyltin oxide and sumarium isopropoxide.

16. The method of claim 1, wherein the transesterification is conducted in the presence of an acidic catalyst.

17. The method of claim 16, wherein said acidic catalyst is selected from the group consisting of p-toluenesulfonic acid, hydrochloric acid, trifluoroacetic acid and Lewis acids.

18. The method of claim 1, wherein the transesterification is conducted in the presence of an alkali metal or alkaline earth metal alcoholate.

19. The method of claim 1, wherein the transesterification is conducted in the presence or an acidic or basic ion-exchange resin.

20. The method of claim 2, wherein the cyanoacrylate formed is an α-cyanoacrylate other than methyl or ethyl cyanoacrylate.

* * * * *